(12) United States Patent
Lindner

(10) Patent No.: US 6,452,156 B2
(45) Date of Patent: Sep. 17, 2002

(54) PROCESS AND SYSTEM FOR THE OPTICAL INSPECTION OF TRANSPARENT CONTAINERS

(75) Inventor: Peter Lindner, Sünching (DE)

(73) Assignee: Krones AG, Neutraubling (DE)

( * ) Notice: Subject to any disclaimer, the term of this patent is extended or adjusted under 35 U.S.C. 154(b) by 24 days.

(21) Appl. No.: 09/826,284

(22) Filed: Apr. 4, 2001

(30) Foreign Application Priority Data

Apr. 6, 2000 (DE) .......................................... 100 17 126

(51) Int. Cl.[7] .................................................. G06M 7/00
(52) U.S. Cl. ............................... 250/223 B; 356/239.1; 356/239.4; 209/522
(58) Field of Search ......................... 250/223 B, 223 R, 250/205, 559.19; 356/239.1, 239.4, 240.1; 209/522, 523, 524, 526

(56) References Cited

U.S. PATENT DOCUMENTS

| | | | |
|---|---|---|---|
| 4,378,493 A | * 3/1983 | Dorf et al. | 250/216 |
| 5,668,887 A | 9/1997 | Parker et al. | 382/108 |
| 6,031,221 A | * 2/2000 | Furnas | 209/524 |

FOREIGN PATENT DOCUMENTS

| | | |
|---|---|---|
| DE | 3532068 | 4/1986 |
| DE | 3407386 | 2/1987 |
| DE | 19512124 | 10/1996 |
| EP | 0 337 421 | 10/1989 |
| GB | 2350424 A | * 11/2000 |

* cited by examiner

Primary Examiner—Kevin Pyo
Assistant Examiner—Stephen Yam
(74) Attorney, Agent, or Firm—Marshall, Gerstein & Borun

(57) ABSTRACT

In a process for the optical inspection of at least partially transparent containers in an inspection area with an illuminating device and a camera for producing images to be evaluated, the degree of transparency of each container is determined, and a light field is configured for this specific container. The light intensity of the light field and/or the imaging sensitivity is adapted to the determined degree of transparency, and the traveling light field is shifted through the inspection area in synchrony with the container. The system for implementing the process has an LED light screen with a plurality of LEDs, which can be activated individually or in groups, and a device upstream of the inspection area for measuring the individual degree of transparency of each container. These components are connected to a control unit, which produces the traveling light field for each container and shifts it in synchrony with the container. The control unit also adapts the light intensity of the traveling light field to the degree of transparency found for the container in question.

20 Claims, 2 Drawing Sheets

PROCESS AND SYSTEM FOR THE OPTICAL INSPECTION OF TRANSPARENT CONTAINERS

FIELD OF THE INVENTION

The invention pertains to a process and system for optically inspecting transparent containers, such as plastic and glass beverages containers.

BACKGROUND OF THE INVENTION

According to DE 3,532,068 C, several bottles a certain space apart are simultaneously inspected optically as they are being conveyed continuously through an inspection area. Each bottle is rotated at least 360° around its longitudinal axis within the inspection area. A single video camera takes partial pictures of the side walls of the bottles at a certain rate and combines them into a single image for each bottle. These images are then examined in an evaluation unit to determine the presence of damage or dirt. The stationary illuminating unit has a light source with a diffuser in front of it. Because the intensity of the light at the two-dimensional opening of the diffuser is the same for all of the bottles passing in front of it and because the bottles can have different degrees of transparency as a result the material of which they are made and/or the wear to which they have been subjected, the brightness of the images produced necessarily varies also, which considerably impairs the quality of the inspection results. Overexposed images are almost impossible to evaluate.

In practice, LED screens are now also being used as illuminating units for the optical inspection of at least partially transparent containers. The LEDs of the light screen are activated jointly and produce light of a certain intensity. An upline measuring device determines the degree of transparency of each container, and the light intensity is adjusted if necessary. If the degrees of transparency of the individual containers differ significantly from each other, however, this adjustment represents only a compromise applicable to the few containers passing through the inspection area.

SUMMARY OF THE INVENTION

The invention is based on the task of providing a process of the general type indicated above and a system suitable for implementing the process, by means of which the containers can be inspected with uniformly high quality regardless of variations in their degrees of transparency.

The task thus defined is accomplished with respect to the process by the features of claim 1 and with respect to the system by the features of claim 8.

According to the process, a traveling light field, which is configured for each individual container, travels along with the container. As a result, each container can be inspected more effectively than it can be with a stationary light field, which is the same for all of the containers being inspected simultaneously. By adapting either the light intensity of the light field on the illumination side and/or the imaging sensitivity on the imaging side to the individual transparency of the container while the container is moving together with its own light field, variations in the degrees of transparency can be compensated in such a way that the image used for the evaluation of one container will be essentially equal in brightness to the image used for the evaluation of another container with a different degree of transparency. As a result, the influence of the individual degree of transparency on the quality of the evaluation is eliminated, and the accuracy of the inspection remains on a uniformly high level.

Because the LED light screen in the device has LEDs which can be activated either individually or in groups, it is possible for a control unit to configure the light field so that it is adapted to each container to be inspected, with this light field then traveling synchronously with the container through the inspection area. The measuring unit determines the individual degree of transparency of each container. Under consideration of the measurement results, the light intensity in the traveling light field can be adjusted so that variations in the degrees of transparency between containers are compensated. This leads to the situation that the camera used for inspection produces images of equal brightness for all containers, regardless of their individual degrees of transparency. There are no longer any significant differences in brightness between the images. Dirt or damage is thus detected with uniformly high quality. Because the individually activated or group-activated LEDs configure a different light field for each container in front of the light screen and because this field travels along with the container, it is easy for several containers to be inspected simultaneously, even though the illumination is adapted individually to each one. The device is especially suitable for the inspection of upright bottles of plastic or glass, the light being either transmitted through the side walls of the container or incident upon them. The bottles can also be rotated around their longitudinal axes during the inspection process if desired. This does not exclude the possibility that the bottom surfaces of the containers or the areas around the mouth are also inspected in the same way. The brightness of the images is selected so that even opaque layers of dirt are recognized, whereas no containers are rejected in error as a result of insufficient brightness.

Because variations in the degrees of transparency are compensated on the illumination side and/or on the receiving side, at least two or more containers traveling in the transport direction a certain distance apart can be inspected simultaneously in the inspection area on a high level of inspection quality.

In a simple process variant, the light intensity in the traveling light field and/or the imaging sensitivity over the height of the image is adjusted to a uniform value for the individual overall degree of transparency of the container. This alone is enough to provide high inspection quality in practical applications in which the degrees of transparency of the containers do not fluctuate significantly in the height direction.

It can also be advisable, however, to determine the variations in the transparency of each container in the height direction and to adapt the light intensity and/or the imaging sensitivity in correspondence with these detected variations.

Under certain conditions, variations in the degree of transparency in the transport direction are also determined and equalized on the illumination and/or on the reception side.

The concomitant motion of the traveling light field and its associated container and the adjustment of the light intensity of this traveling light field to the individual degree of transparency of the container can be easily implemented in terms of the process technology involved by means of an LED light screen consisting of a plurality of LEDs, which can be activated either individually or in groups. It is advisable for the LEDs to be activated in rows parallel to the axis of the container. It is especially favorable for the illumination to be continuous.

The adaptation of the light intensity in the traveling light field for the purpose of equalizing the variations in the degree of transparency or for adapting the intensity to the individual degree of transparency can be easily accomplished in terms of the process technology involved by adjusting the current strength and/or the flash time and/or the number or distribution of the activated LEDs.

To increase the inspection quality even more, it can be advisable to vary the light intensity and/or the imaging sensitivity also as a function of the transport position and/or the rotational position of each container in the inspection area. For example, the actual distance between the container and the camera can be a parameter of such variation, or, in the case of a container which is not round, the rotational position during imaging in relationship to the camera can be used as a parameter. The information required to take these parameters into account can be easily defined in terms of the process technology involved by appropriate sensors or stored programs.

With respect to the system, the control device is designed in such a way that it configures the light field on the LED light screen for each container and moves it through the inspection area together with the container. The compensation device uses the information it receives from the measuring device to adjust the light intensity in the traveling light field accordingly. The control device and the compensation device work together to ensure that the images are uniformly bright regardless of the variations in the degrees of transparency.

It is advisable for the control device and the compensation device to be combined into a common electronic control unit, to which the measurement results of the measuring device and, for example, the position and velocity of each container in the inspection area are transmitted in the form of signals.

If the automatic control is based on an average degree of transparency, a simple measuring device with essentially only a single light source and a measurement signal receiver is all that is required.

In the case that the transparency profile of the container is measured and factored into the adjustment of the light intensity or imaging sensitivity, a measuring device in the form of a linear measuring array with several measuring cells and measuring sections and possibly several light sources can be favorable. To obtain this profile information, different brightnesses in the measuring cells, for example, or different light intensities of the light sources required to achieve equal brightnesses at the measuring cells are taken into account.

In a simple embodiment, the LEDs in the LED light screen can be activated in rows parallel to the axis of the container. The traveling light field can be configured by one or more rows; all the LEDs in one row do not necessarily have to be activated.

The light intensity of the traveling light field can be adjusted to the measured degree of transparency or to the transparency profile by making the appropriate changes to the current strength and/or the flash time. It is also possible, however, to vary the number and/or the distribution of the activated LEDs.

Because of the demand for uniformly high inspection quality and because of the high container transport velocities normally used in modem machines, it is advisable for at least one microprocessor with appropriate programmability to be present in the control unit.

The microprocessor can have a program memory section, where parameters used repeatedly during the adjustment of the light intensity and/or of the imaging sensitivity can be stored for a certain type of container. This is an especially effective measure in cases where a simple measuring device is provided to determine merely an average degree of transparency and where an average container transparency profile is known.

The device is especially suitable for the inspection of the side walls of glass or plastic bottles according to the transmitted light or incident light principle. It is also conceivable, however, that the bottoms or mouths of the bottles could also be inspected.

BRIEF DESCRIPTION OF THE DRAWINGS

An exemplary embodiment of the object of the invention is explained below on the basis of the drawings.

DESCRIPTION OF THE PREFERRED EMBODIMENT

Figure 1:
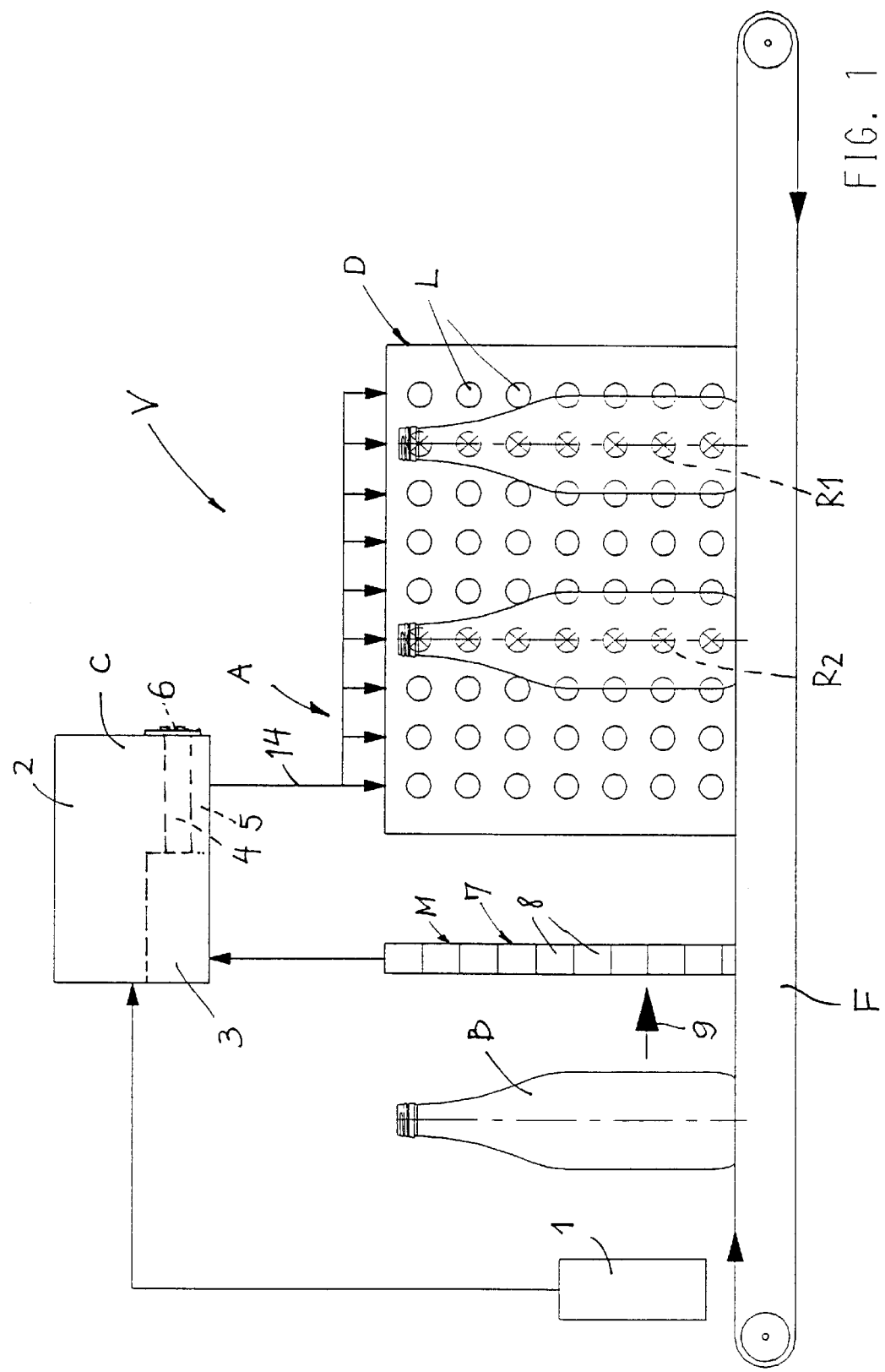
FIG. 1 is a schematic diagram of a vertical cross section through a system for the optical inspection of containers, extending longitudinally with respect to the transport direction.
Figure 2:
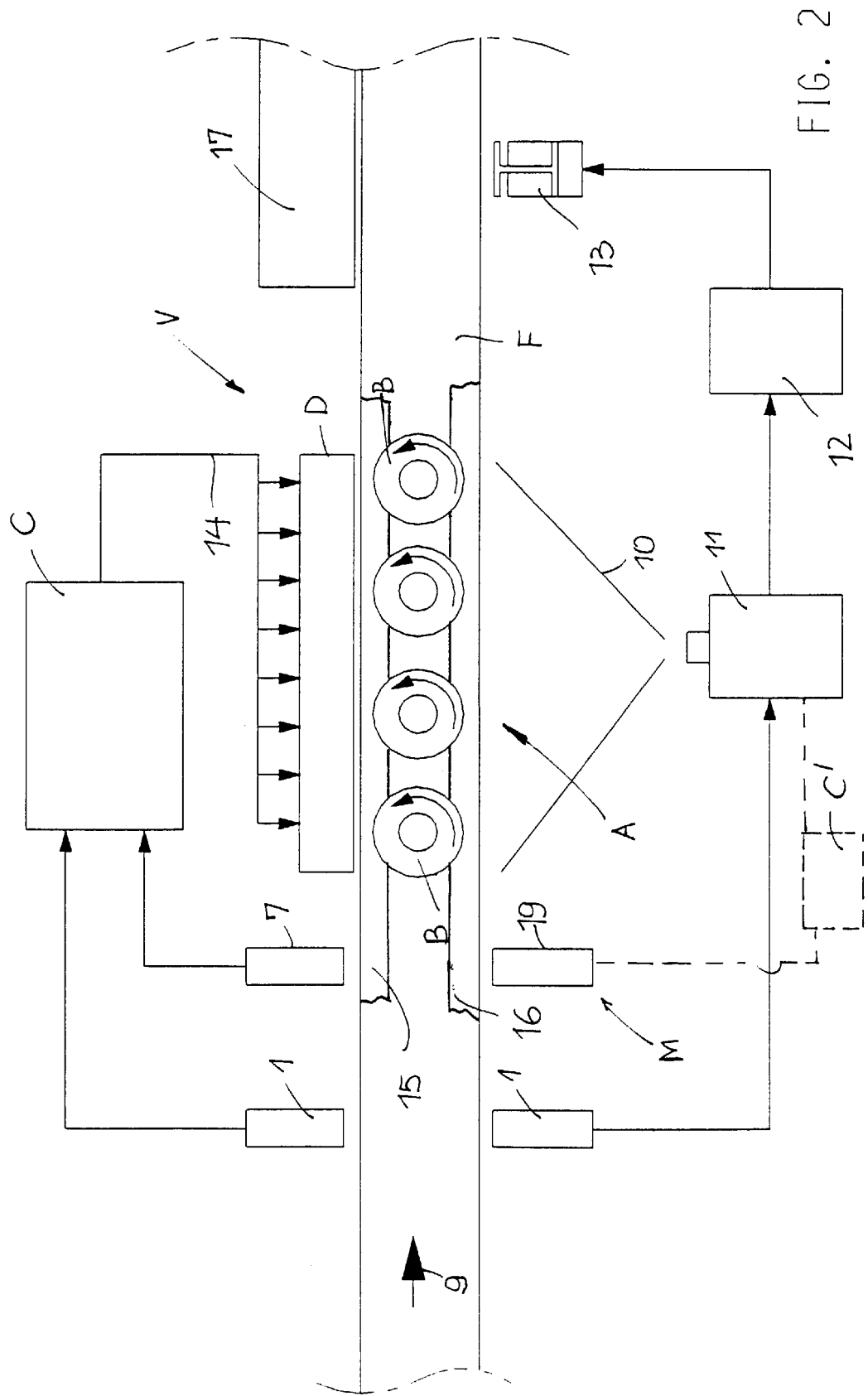
FIG. 2 is a schematic view of the system according to FIG. 1, looking down from above.

A system V, shown schematically in FIGS. 1 and 2 in vertical cross section and a top view, respectively, for the optical inspection of containers B, has an inspection area A, through which a straight transport device F passes, which can be driven in the direction of the arrow 9 in what amounts essentially to continuous motion. Upstream of the inspection area A there is a sensor 1, which measures the transport distance traveled or the transport velocity, and which is connected to a control unit C and to a CCD camera 11, which is aimed at the inspection area A, so that it can transmit signals to them. In addition, a measuring device M is provided upstream of the inspection area or even in this area, which, in the embodiment shown here, consists of a constant light source 19 and, facing it, a linear measuring array 7, consisting of several measuring cells 8, arranged in a vertical stack. The measuring device M is also connected to the control unit C.

The containers B are bottles of plastic or glass, for example, and are therefore at least partially transparent. With a sufficient distance allowed between them, they are transported at a sufficient transport velocity through the inspection area A. In the embodiment shown here, at least two containers are present at any one time in the inspection area A. It would also be possible, however, for more than two containers to be inspected simultaneously or possibly for only one to be inspected at a time. During the inspection, the containers B are rotated around their longitudinal axis by means of, for example, two conveyor belts 16, 15 of the transport device, which travel at different speeds.

Opposite the CCD camera 11 is at least one stationary LED light screen D, which serves as the illumination device. It consists of a plurality of LEDs L, which can be activated either individually or in groups. An auxiliary device 10 (not shown in detail) can be set up in front of the lens of the CCD camera 11 so that the CCD camera 11 can generate images of the containers along the entire inspection area A, as is standard practice.

In the control unit C there is a control device 2, by means of which a light field can be generated from a specific number of activated LEDs L, this field being configured for a specific container B. In correspondence with the signals being received from the sensor 1, a driver device 14, for example, shifts this field across the LED light screen D, thus creating a traveling light field which moves at the same speed as the container. In addition, the control unit C also includes a compensation device 3, which adapts the light intensity in the traveling light field to the degree of transparency of the specific container B in question, this transparency having been determined previously by the measuring device M. The control unit C also comprises at least one microprocessor 4 and a memory unit 5, into which certain parameters can be programmed. An input or display field 6 for the control unit C can also be provided.

The CCD camera 11 is connected to an evaluation circuit 12, in which the images derived from the containers are evaluated in order to determine whether any of the containers are damaged and/or dirty. A stored reference image can be used for this purpose, for example. If a damaged or dirty container B is found, it is separated from the other containers downstream of the inspection area A. For this purpose, the evaluation circuit 12 is connected, for example, to an ejector 13, which it can actuate.

The light field which has been assigned to each container B and configured individually for it is, for example, formed by at least one row R1, R2 of LEDs L, parallel to the axis of the container in question (FIG. 1). It would also be possible, however, for the LEDs to be activated in some other pattern such as a group conforming to the contours of the container. By successive activation in the transport direction 9, e.g., of one row in each case, the row R1, R2 of activated LEDs L configuring the light field travels in the transport direction in synchrony with the container B. At uniform intervals the CCD camera 11 generates partial images of each container B, which is rotated at least once around its longitudinal axis as it passes by. The partial images are combined into a single image for each container and then evaluated.

The light intensity of the concomitantly moving light field is adapted to the degree of transparency of the container in such a way that the images produced by the CCD camera are of approximately equal brightness, regardless of variations among the measured degrees of transparency of the individual containers. For example, for a container which is darker than the others, that is, which is less transparent, the light intensity is increased and vice versa. This can be accomplished by the automatic control of the current strength and/or of the flash time and/or of the change in the number (per unit of area) of groups of activated LEDs L.

Because the measuring device M shown here is made up of separate measuring cells 8, it measures a transparency profile for the container in question. This profile could show, for example, a lower degree of transparency in the shoulder and mouth area of the container and a higher degree of transparency in the main body area of the container. In accordance with this transparency profile, the compensation device 3 varies the light intensity over the height of the container in such a way that the container, through which light has been transmitted or upon which light has fallen, appears equally bright to the CCD camera 11 over its entire height. It is conceivable that the measuring device could be designed in such a way that it measures variations in the degree of transparency in the transport direction, so that the light intensity in the traveling light field can also be varied in the transport direction. If a measuring device is provided with a light source and only one measuring cell, which means that the measuring device measures only an average degree of transparency for the container in question, then a previously determined transparency profile can be stored in the program of the microprocessor 4 or in the memory unit 5; the automatic control of the light intensity of the light field is then based on this stored profile.

FIG. 2 shows in broken line another control unit C', which is connected to the measuring device M and also to the CCD camera 11. The control unit C' can be designed in the same way as the control unit C. With this second unit, it is possible to vary the imaging sensitivity for each container B on the camera side in correspondence with the measured degree of transparency, so that images of approximately equal brightness are produced even for containers with different degrees of transparency. In the case of CCD cameras with a 2-dimensional array, the regions of pixels assigned to the individual containers can be varied in their sensitivity in correspondence with the movement of the container. The two measures, i.e., adapting the light intensity of the LEDs L and modulating the imaging sensitivity for each container, can be taken in combination either alternatively or additively.

The system V shown here serves, for example, to inspect the containers (bottles) B either by means of light which is transmitted through or incident upon the side walls. In modified form, the system can also be used to inspect the bottoms or the mouths or the sealing surfaces or to inspect only these areas. The transport direction F is shown proceeding in a straight line. As an alternative, the transport device could also be circular, etc. The LEDs L are preferably activated row by row, the vertical rows thus succeeding each other in the transport direction in order to generate the traveling light field moving together with the container. The traveling light field could also be generated, however, by the actuation of individual LEDs L. The adjustment of the light intensity and/or of the imaging sensitivity is accomplished in such a way that images of approximately equal brightness are generated, the brightness of which is so high that even the smallest possible areas of damage or opaque areas or dirt on or in the containers can be reliably detected. In a departure from the exemplary embodiment just described, it is also possible to use several cameras, in which case each camera is assigned to an individual container and follows its movement by means of controlled pivoting mirrors (DE 3,407,386 C2).

If the equalization or compensation of the degrees of transparency is accomplished by adjusting the light intensity of the traveling light field for each container, then it is possible to work with a fixed exposure time and a fixed exposure setting of the CCD camera.

The sequence of events according to the process of the invention is as follows:

The measuring device M measures the individual degree of transparency of each container B, either as an average degree of transparency or in the form of a transparency profile. The information thus obtained is used in the control unit C to control the light intensity of the light field which has been configured for this container upon its arrival in the inspection area A in such a way that the CCD camera 11 sees all the containers at one selected brightness level, which is independent of the individual degrees of transparency. The light field configured for the container moves as a traveling light field across the LED light screen D in synchrony with the container in question. The container is rotated around its longitudinal axis as it travels. The CCD camera 11 produces partial images of each container at certain intervals as the container travels through the inspection area A. The partial images are combined into a single image of the container and evaluated in the evaluation unit 12 and compared with a reference. If the evaluation indicates the presence of damage or dirt, the ejector 13 is actuated to remove the container in question at the proper moment and to transfer it to a discharge conveyor belt or to a collection bin 17. The images can also be automatically controlled so that they are all of approximately the same brightness by the auxiliary use of the control unit C' on the imaging side, or they can be controlled only by the use of traveling light field on the imaging side.

Because each container to be inspected or each of several containers to be inspected simultaneously has its own individually configured light field, which travels along with it, a high degree of freedom for managing the inspection process by both open-loop and feedback control techniques is inherent in the process, so that the effects of different degrees of transparency or transparency profiles on the brightness of the images can be eliminated and the inspection quality can be increased. The changeover from a stationary light field to individual traveling light fields for the containers as they are being inspected assumes that an illumination device with precise open-loop and feedback controls is available. This requirement can be satisfied in optimum fashion by at least one LED light screen, which has LEDs D, which can be activated either individually, in groups, or in rows, the light intensity of which can be varied quickly enough by adjustment of the current strength and/or the flash time and/or the distribution of the activated LEDs L. Microprocessor control and the performance capacity of the LED light screen, at least one of which is provided, make it possible to conduct the inspection process at the high frequency absolutely necessary for modern systems of this type, especially when they are integrated into high-speed container handling processes and/or work together with other high-speed systems.

I claim:

1. Process for the optical inspection of a succession of at least partially transparent containers traveling through an inspection area, in which process the containers are exposed to light from an illuminating device and images of at least parts of the container are produced and evaluated, comprising the following steps:

determining the individual degree of transparency of each container;

configurating a light field for this container;

adjusting the light intensity of the light field or the imaging sensitivity to suit the determined degree of transparency of the container; and shifting the light field is shifted as a traveling light field through the inspection area synchronously with the container so that images of essentially uniform brightness are produced for containers with different degrees of transparency.

2. Process according to claim 1, and the steps of inspecting at least two containers a certain distance apart in the transport direction simultaneously in each case, and illuminating each of the containers by a traveling light field individually adapted to its degree of transparency.

3. Process according to claim 1, adjusting the light intensity in the light field or the imaging sensitivity over the height of the image to a uniform value to represent the overall transparency of the individual container.

4. Process according to claim 1, the steps of determining variations in the degree of transparency present over the height of the container and variably adjusting the light intensity in the light field or the imaging sensitivity in correspondence with the variations over the height of the container thus found.

5. Process according to claim 1, and the step of determining variations in the degree of transparency of the container which are present in the transport direction, and adjusting the light intensity in the light field or the imaging sensitivity within the width of the configured light field looking in the transport direction in correspondence with the determined variations.

6. Process according to claim 1, and the steps of designing the illuminating device as an LED light screen with a plurality of LEDs assigning a traveling light field to a container, configuring the traveling light field in question by the activation of a succession of LEDs proceeding in the transport direction, and making the configured field into a traveling light field by the successive activation of LEDs which traveling a light field is shifted across the LED light screen in synchrony with the assigned container.

7. Process according to claim 6, and the step of adapting the light intensity in the light field to the degree of transparency by adjustment of the current strength or the flash time or the number or distribution of the activated LEDs in the group.

8. Process according to claim 1, and the step of varying the light intensity in the light field or the imaging sensitivity as a function of the transport position or as a function of the rotational position of the container in the inspection area.

9. In a system (V) for the optical inspection of at least partially transparent containers (B), with a continuously operating container transport device (F) passing through the inspection area (A), with an illuminating device directed at the containers (B) in the inspection area (A), and with at least one electronic camera (11), which is connected to an image evaluation device (12), the improvement comprising that the illuminating device has an LED light screen (D) with a plurality of LEDs (L), which are activated individually or in groups to create a traveling light field; that, upstream of the inspected area (A), a measuring device (M) is installed to measure the individual degree of transparency of each container (B); and that said LED light screen (D) is connected to a device (2) for controlling said traveling light field and to a device (3) for compensating for differences in transparency of the containers.

10. System according to claim 9, wherein said individual LEDs or groups of LEDs (L) can be activated in succession in the transport direction (9) by the control device (2) to configure a said traveling light field moving in synchrony with each container (B), and the light intensity of the activated LEDs (L) can be adjusted by said compensation device (3) in correspondence with the measured degree of transparency of the container in order to obtain images of essentially the same brightness for containers of different degrees of transparency.

11. System according to claim 9, wherein the containers (B) are a certain distance apart in the transport direction (9); the inspection area (A) is at least as long as the distance marked out by two successive containers (B) so that at least two containers (B), which are following each other in the transport direction (9) and which are being rotated during the inspection, can be inspected simultaneously; said control device (2) can control as many said traveling light fields as there are containers (B); and said compensation device (3) can adjust the light intensity of each said traveling light field assigned to a container individually to the degree of transparency of that container.

12. System according to claim 9, wherein said control device (2) and said compensation device (3) are combined into a control unit (C), which is connected to said measuring device (M) and to a position and transport speed sensor (1) so that it can receive signals from them.

13. System according to claim 9, said measuring device (M) has a light sensor with an essentially point source of light (19) and a measurement receiver (7) for determining an average degree of transparency of the container in question.

14. System according to claim 9, wherein said measuring device (M) has a linear brightness measuring array (7) oriented approximately in the direction of the container axis and consisting of several separate measuring sections (8) and/or several light sources for determining a transparency profile.

15. System according to claim 9, wherein said LEDs (L) in said LED light screen (D) can be activated in rows parallel to the container axis.

16. System according to claim 9, wherein the current strength or the flash time for the activation of the LEDs (L) can be changed.

17. System according to claim 12, wherein said control unit (C) contains at least one microprocessor (4).

18. System according to claim 17, wherein said microprocessor (M) is associated with a program memory unit (5), in which parameters corresponding to a transparency profile of the containers can be stored.

19. System according to claim 9, wherein the system (V) for inspecting containers is with the light transmitted through the side walls of the containers.

20. Process according to claim 6, and activating rows of LEDs parallel to the axis of the container or of selected groups of LEDs.

* * * * *

UNITED STATES PATENT AND TRADEMARK OFFICE
CERTIFICATE OF CORRECTION

PATENT NO.    : 6,452,156 B2
DATED         : September 17, 2002
INVENTOR(S)   : Peter Lindner It is certified that error appears in the above-identified patent and that said Letters Patent is hereby corrected as shown below:

<u>Column 7,</u>
Line 48, "is shifted" should be deleted.
Line 58, "claim 1, adjusting" should be -- claim 1, and adjusting --.
Line 62, "claim 1, the steps" should be -- claim 1, and the step --.

<u>Column 8,</u>
Line 33, "LEDs (L)," should be -- LEDs (L).
Line 43, "by the control device" should be -- by said control device --.
Line 46, "activated LEDs" should be -- activated said LEDs --.

<u>Column 9,</u>
Line 9, "and/" should be deleted.
Line 15, "activation of the LEDs" should be -- activation of said LEDs --

Signed and Sealed this

Seventeenth Day of December, 2002

JAMES E. ROGAN
*Director of the United States Patent and Trademark Office*